United States Patent [19]
Lemieux et al.

[11] Patent Number: 6,165,251
[45] Date of Patent: Dec. 26, 2000

[54] ON-LINE GAS CHROMATOGRAPH WITH SAMPLE PREPARATION, CONCENTRATION, AND CALIBRATION APPARATUS FOR MEASURING TRACE ORGANIC SPECIES FROM COMBUSTOR FLUE GAS

[75] Inventors: Paul M. Lemieux, Cary; Jeffery V. Ryan, Chapel Hill; William T. Preston, Raleigh, all of N.C.

[73] Assignees: The United States of America as represented by the Administrator of the U.S. Environmental Protection Agency, Washington, D.C.; Arcadis Geraghty-Miller, Inc., Denver, Colo.

[21] Appl. No.: 09/304,827

[22] Filed: May 5, 1999

Related U.S. Application Data

[60] Provisional application No. 60/084,496, May 5, 1998.

[51] Int. Cl.[7] .................................................. B01D 53/02
[52] U.S. Cl. ..................................... 95/82; 95/87; 96/101; 96/105
[58] Field of Search ................................ 73/23.35, 23.41; 95/82, 87, 89; 96/101–103, 105, 106

[56] References Cited

U.S. PATENT DOCUMENTS

| | | | |
|---|---|---|---|
| 4,003,257 | 1/1977 | Fletcher et al. | 95/87 X |
| 4,500,432 | 2/1985 | Poole et al. | 95/82 X |
| 4,774,190 | 9/1988 | Weiss | 95/87 X |
| 4,805,441 | 2/1989 | Sides et al. | 96/106 X |
| 5,047,073 | 9/1991 | Sletter et al. | 95/82 X |
| 5,402,668 | 4/1995 | Murakami et al. | 95/87 X |
| 5,762,686 | 6/1998 | Borzio | 95/82 |
| 5,827,353 | 10/1998 | O'Neil | 95/87 |
| 5,861,316 | 1/1999 | Cage et al. | 95/82 X |

Primary Examiner—Robert H. Spitzer
Attorney, Agent, or Firm—Lorusso & Loud

[57] ABSTRACT

Apparatus and method for periodic analysis of trace amounts of volatile organic compounds in a waste gas provide for feeding of a sample of a waste gas first to an organics concentrator which isolates the volatile organic compounds from the waste gas sample and prepares a concentrated sample for feed to a gas chromatograph. In normal operation, a waste gas is continuously sampled from the waste gas source to produce a continuous waste gas flow through a switching valve and out a vent. A portion of that waste gas flow is periodically diverted by the switching valve and routed to the organics concentrator. The switching valve also receives calibration samples containing known concentrations of the volatile organic compounds prepared in a gas blender. It periodically feeds the calibration samples to the organics concentrator and the gas chromatograph for calibration of the system.

16 Claims, 1 Drawing Sheet

ON-LINE GAS CHROMATOGRAPH WITH SAMPLE PREPARATION, CONCENTRATION, AND CALIBRATION APPARATUS FOR MEASURING TRACE ORGANIC SPECIES FROM COMBUSTOR FLUE GAS

This application claims priority of applicants' provisional application of the same title, serial No. 60/084,496, filed May 5, 1998, the teachings of which are incorporated herein by reference.

BACKGROUND OF THE INVENTION

1. Field of the Invention

This invention relates to the monitoring of concentrations of volatile organic compounds (hereinafter, VOCs) present in trace amounts (ppb) in waste gases, inclusive of combustion exhaust gases and incinerator effluents.

2. The Prior Art

The U.S. Environmental Protection Agency's (EPA) current regulatory approach for combustion and incineration sources emphasizes the real-time monitoring of trace process emissions including particulate, metals, and volatile, semivolatile, and nonvolatile organic compounds. Continuous emission monitors (CEMs) are needed to indicate emissions compliance, evaluate combustion process performance, and optimize process operation on a more timely, continuous basis. Unfortunately, the CEM technologies to support this approach have not been thoroughly developed and/or demonstrated. The ability to measure volatile organic compounds (VOCs) on a near-real-time basis is also valuable to research examining the formation and control of volatile organic products of incomplete combustion (PICs) from thermal treatment processes. The ability to measure VOCs on a near-real-time basis is also valuable to such important research which should be conducted in as short a time frame as possible.

A need also exists for a near-real-time indicator of combustion/incineration performance as a monitor of surrogate VOCs that may be indicators of dioxin emissions, considered to be the most toxic pollutant produced from combustion sources and as an inexpensive tool to screen combustion sources for hazardous air pollutants (HAPs).

Fourier Transform Infrared (FTIR) spectroscopy, is capable of making such measurements, but not with the sensitivity needed to measure typical PIC levels found in real-world systems.

Gas Chromatography (GC) is a mature technology that can be used to separate and identify trace compounds. However, a standard GC was found to have insufficient sensitivity with which to measure the PICs, which are present down to the 1 part per billion (ppb)concentration.

SUMMARY OF THE INVENTION

Accordingly, it is an object of the present invention to provide an apparatus and method with sufficient sensitivity to measure concentrations of VOCs present as trace amounts as low as 1 ppb, in waste gases, in order to monitor compliance with current regulatory clean air standards.

Accordingly, the present invention provides an apparatus for analysis of trace amounts of volatile organic compounds in a waste gas, which apparatus includes a gas probe for mounting with its opening within a stream of the waste gas. The apparatus further includes an organics concentrator containing a sorbent having a preferential affinity for the volatile organic compounds. A waste gas line connects the gas probe to a first vent line through a switching valve. The switching valve, in a sampling mode, is positioned to divert a portion of the waste gas flowing to the vent to the organics concentrator for passage through a sorbent contained in the gas concentrator in a first direction. The waste gas is depleted of its VOC content as the VOCs are removed therefrom by the sorbent and is exhausted through a second gas vent. A source of carrier gas feeds a carrier gas through the sorbent of the gas concentrator, in a second direction, opposite the first direction, to purge the VOCs from the sorbent thereby forming a concentrated sample. A gas chromatograph receives the concentrated sample and analyzes same to determine concentrations of the VOCs. A gas blender blends at least one VOC in different amounts with a carrier gas to form, in succession, a plurality of calibration samples. Calibration gas lines route the calibration samples either to the switching valve and/or optionally, to a three-way valve adjacent the gas probe.

The method of the present invention is a process for analyzing a waste gas stream to determine concentrations of VOCs contained in the waste gas. The waste gas stream is sampled to establish a continuous waste gas flow through, in sequence, the waste gas line, switching valve and a first vent line. A portion of the waste gas flow is periodically diverted at the switching valve and the diverted portion of the waste gas is fed, in a first direction, through a sorbent in an organics concentrator which preferentially desorbs the VOCs, and vents the remainder of the waste gas flow through a second vent line, essentially free of the VOCs. The feed of the current waste gas flow is periodically discontinued and a carrier gas is routed through the sorbent in a second direction, opposite of the first direction, for desorbing the VOCs from the sorbent, thus forming a concentrated gas sample. The concentrated gas sample is fed to a gas chromatograph and analyzed therein to determine concentrations of the various VOCs. For calibration, various amounts of at least one VOC are admixed with the gaseous carrier to form calibration samples containing known concentrations of the VOC. These calibration samples are periodically fed through the sorbent in the organics concentrator. The VOCs preferentially absorbed onto the sorbent in the organics concentrator are stripped therefrom by introducing a carrier gas in the reverse direction through the sorbent to form concentrated calibration samples which are fed to the gas chromatograph for analysis and calibration of the apparatus.

One advantage of the present invention is that it is able to achieve several orders of magnitude better sensitivity than is normally obtainable by running the stack gas sample directly into a GC. In addition, the apparatus of the present invention can operate on samples taken directly from the hot, wet, acid gas laden regions of a combustion device if necessary.

BRIEF DESCRIPTION OF THE DRAWINGS

The sole drawing FIGURE is a schematic view of a preferred embodiment of the analytical apparatus of the present invention.

DESCRIPTION OF THE PREFERRED EMBODIMENTS

Figure 1:
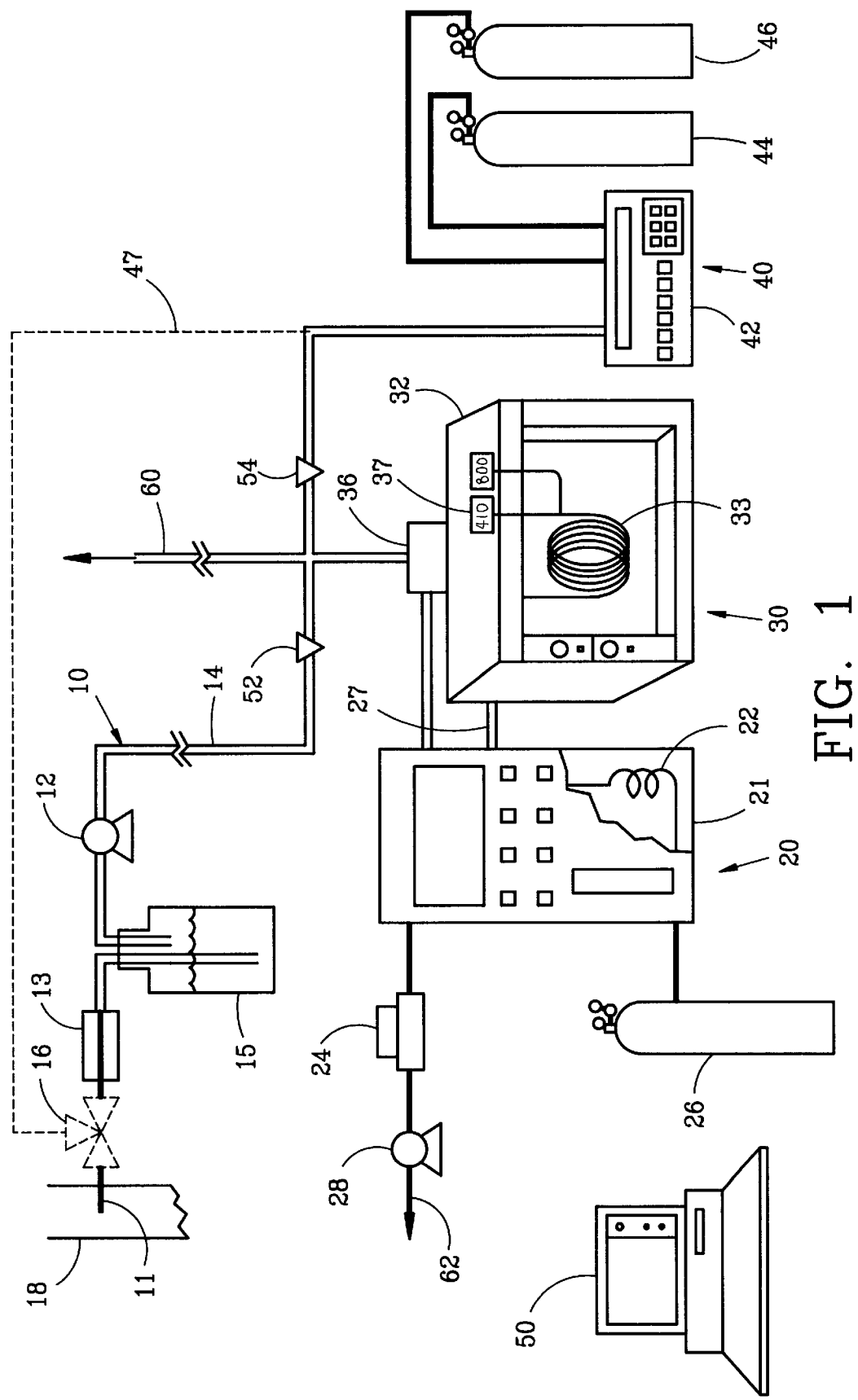

As seen in the drawing FIG. 1 the analytical system of the present invention includes a heated sample delivery/sample conditioning system 10, a purge and trap sample concentrating unit 20, a gas chromatograph analyte separation/detection unit 30, and a gas blending calibration unit 40. A diagram of the OLGC CEM is presented in FIG. 1.

The sample delivery/sample conditioning system 10 nominally consists of a short length of heat-traced (115° C.), 0.64 cm (¼ in) O.D. stainless steel tubing that serves as the sample probe 11. A heated (115° C.) low pressure drop, particulate filter 13 is located between the probe 11 and a heated (120° C.) sample pump 12. The effluent of the sample pump 12 is routed to the sample manifold through 0.64 -cm O.D. Teflon heat-traced (150° C.) sample lines 14 ("waste gas line"). Nominal flow through the system is 10–15 L/min. For highly acidic measurement environments, an optional impinger 15 containing approximately 1 L of deionized water can be used as a gas scrubber with periodic replacement with fresh/clean deionized water. Also optional is a 3-way valve 16 for introducing a calibration sample from the gas blending calibration unit 40.

In normal use, a portion of the waste gas flowing through stack 18 is continuously sampled through probe 11 and a continuous flow of the sample waste gas is established through waste gas line 14, through valve 52 and out vent 60. For sampling, e.g. during a 10 minute interval recurring every hour, 10–20% of the sampled waste gas is diverted through switching valve 36 to organics concentrator 21, while the remainder of the waste gas (80–90%) is exhausted through vent 60.

The purge and trap sample concentrating unit 20 includes sample concentrating device 21 ("organics concentrator") which is a Tekmar LSC-2000 thermal desorption unit that has been modified to accommodate the collection of combustion samples directly. The modification is in addition of a vacuum pump 28 to the outlet of device 21 and connection of its inlet to a switching valve 36. Switching valve 36 is a heated (220° C.), electrically controlled, pneumatically actuated, 6-port valve which directs flow in a first direction to the sorbent 22 in the organics concentrator 21 at the time of sampling. In the sample position, a slipstream of the waste gas stream in stack 18 is drawn through a sparge vessel 15 ("gas scrubber") containing 5 mL of deionize water to the inlet of the cryogenically cooled sorbent column (trap) 22, under vacuum and at a constant flow rate, by the vacuum pump 28. Flow rate is regulated by a mass flow controller 24 located at the exit of the sorbent column 22. Total sample volumes are nominally 500 $cm^3$. Following sampling, the 6-port switching valve 36 is returned to the bypass position, the sorbent trap 22 ballistically heated to 250° C., and the effluent diverted to the gas chromatograph (hereinafter "GC") 32 through line 27. With the valve 36 in the bypass position, a nitrogen carrier from bottle 26 is routed through the purge gas controller internal to the organics concentrator 21, through valve 36 and into the sorbent column 22. Valve 52 is normally open and valve 54 is normally closed to allow periodic sampling of the waste gas.

The GC 32 is a HP 5890 series II GC equipped with both a flame ionization detector 37 ("FID") and an electron capture detector 38 ("ECD"). The VOCs transferred to the GC are refocused onto the head of the analytical column by cooling the GC oven to subambient temperatures. Once the VOCs have been refocused, the GC oven temperature increases over a set temperature program to resolve target analytes of interest. VOCs are separated by an Rtx-624 0.53 mm ID×75 m fused silica capillary column (Restck Corp., 3.0 mm film thickness) 33. The effluent of the column 33 is split to deliver sample to both the FID and ECD simultaneously (ratio 9:1, respectively).

A computer-based data station 50 is used to process detector signals into units proportional to gas concentration. This data station 50 also controls all automated systems including starting/stopping pumps 12,28, actuating gas switching valves including switching valve 36, and generating data reports.

The mass flow controlled-based gas blending/dilution system 40 allows the calibration gas to be sampled directly, in the same manner as an actual waste gas sample. Sampling the gas directly eliminates: the uncertainty associated with syringe injection, the need to measure total volume samples, and the need to relate measured mass to volume sampled. As long as the volume sampled remains constant, all measurements are made directly in the desired concentration units (either ppbv or $\mu g/m^3$).

The gas blending calibration unit 40 includes a gas blender 42, a VOC gas blend source, i.e bottle 44, and a carrier gas source such as bottled nitrogen 46. The contents of bottles 44 and 46 are selectively mixed within the gas blender 42 to form, in sequence, gas samples containing a range of concentrations for the VOC blend. For purposes of calibration, valve 52 is closed and valve 54 is open to allow the gas samples to enter the organics concentrator 21, more specifically, to the same end of sorbent column 22 which receives the waste gas samples, for flow through the sorbent column 22 in a first direction for absorption of the VOCs from the sample gas onto the sorbent. In the same manner that concentrated sample containing VOCs derived from the waste gas are fed to gas chromatograph 32, after reaching steady state absorption of the VOCs onto the sorbent, valve 36 cuts off flow of the sample gas and a carrier gas such as nitrogen is introduced from 26 in the reverse direction through the sorbent column 22 to desorb the VOCs and to thereby form a concentrated sample gas fed to the chromatographic column 33 in gas chromatograph 32 through line 27.

While the calibration gas is normally sampled at the switching valve 36, it can also be introduced through line 47 at three-way valve 16, located adjacent probe 11. By calibrating the system with the calibration gas sample introduced through three-way valve 16, it becomes possible to correct for any residual VOCs which might adhere to or otherwise accumulate within the system. Thus, the three-way valve 16 switches between a sampling position and a calibration position. In the sampling position, the waste gas from stack 18 is admitted to the waste gas line 14 with line 47 blocked. In the calibration position waste gas from probe 11 is blocked and line 47 is in communication with line 14 to allow the calibration gas samples to enter the system.

Experimental

VOC measurements were made on the EPA's pilot-scale rotary kiln incinerator simulator (RKIS). This combustion test facility has been described in detail, for example, by Lemieux, P. M., J. V. Ryan, C. Lutes and K. Bruce, "Interactions Between Bromine and Chlorine in a Pilot-Scale Hazardous Waste Incinerator," in Proceedings of International Conference in Incineration and Thermal Treatment Technologies, Savannah, Ga., May 1996. This system was built for use in the EPA's hazardous waste incineration research program. As such, it was designed to be able to handle hot, wet, particulate-containing, acid-gas-laden samples taken directly from the EPA's research combustors prior to any flue-gas cleaning equipment. Emissions measurements were made to characterize volatile PICs while feeding a chlorinated and/or brominated surrogate waste. The optional water gas scrubber 15 was used during these tests. Emissions measurements were made upstream of any pollution control devices. The acid gas levels at the measurement location approached 3% v/v. Several (2 to 3) 10-minute on-line measurements were made during the course of each test. The system was operated daily over a 2-week period. Pre- and post-test zero and span checks were performed to verify emissions measurement performance. The calibration gas was also measured from the probe (introduced at valve 16) to establish system bias.

The calibration was performed by relating compound concentration to respective detector responses (area counts) using a least square linear regression. The quality of the linear relationship is evidenced by the correlation coefficient or "r" value. The respective area counts are then used to calculate a "measured" concentration. This measured concentration is then compared to the actual concentration at each calibration point to evaluate overall approaches by which CEM performance is commonly evaluated.

The calibration of the apparatus was performed in general accordance with EPA Method 25A. A 4-point calibration was conducted (zero, span, 2 mid-points) with calibration quality a function of deviation from either full scale (FS) or gas concentration. A 25-component VOC gas blend from bottle 44 (FIG. 1) (nominal concentration 260 ppbv) was diluted with nitrogen from bottle 46 to achieve desired VOC concentrations by gas blender 42. The components of the VOC gas mix are presented in Table 1. The VOCs targeted include primarily brominated and chlorinated alkanes/alkenes as well as several aromatics with boiling points ranging from −23.7 to 180.5° C. The VOCs targeted for measurement were specific to research needs, and are not all inclusive of the list of potential VOCs capable of being measured by this system. As noted above, the calibration gas is normally sampled at the switching valve 36, but can also be introduced through line 47 and 3-way valve 16 at the probe 11. Sampling at the switching valve 36 minimizes the consumption of the calibration gas by a factor of at least 25.

The results of the 4-point calibration, with calibration error expressed as a function of FS (absolute error) and as a function of gas concentration (relative error), are presented in Tables 2 and 3, respectively. Examining calibration error as an absolute function, with the exception of tetrachloroethylene, maximum calibration error was less than 5% of FS (100 ppbv) or 5 ppbv. Although greater than the Method 6C requirement of $\leq \pm 2\%$ FS, the calibration error achieved is excellent for measurements at least a factor of 1000 lower than those intended by the above measurement methods. Similarly, examining calibration error as a relative function, with the exception of tetrachloroethylene, maximum calibration error was $\leq \pm 16\%$ of the gas concentration. Maximum relative calibration error was observed, not surprisingly, at the lowest calibration concentration. However, on an absolute basis, little calibration error difference exists across all 4 data points. This further supports the inappropriateness of using relative error as a criterion for assessing measurement performance.

Tables 2 and 3 also include the calibration linear regression analysis correlation coefficient for each VOC. This coefficient, or "r" value, is one of the performance criteria presented in EPA Performance Specification 9. Eleven of 23 compounds met or exceeded the calibration performance specification requirement of 0.995.

EPA Performance Specification 9 also requires each calibration level or concentration to be measured in triplicate. This calibration precision requires that each point be within 5% of the average. Table 4 presents the relative percent difference from the average for triplicate runs of the 30 ppb calibration point. Only 5 of the 23 target compounds met this criterion. It appears that Run 1 had the most overall impact on calibration point precision. This table illustrates the inconsistency in precision not only over the 3 runs, but also between compounds. This systematic imprecision likely contributed negatively to the overall quality of the multi-point calibration.

Another measurement performance parameter is system bias. A system bias check is commonly performed when calibration gases are delivered to the CEM in a manner that differs from how actual sample streams are measured. This check verifies that the sample delivery system is inert and free of leaks and contaminants. The system bias check is performed by introducing the calibration and/or zero gas directly to the CEM and then at the stack (at three-way valve 16) through the entire sample delivery system and comparing the measured responses. Table 5 presents the results of a system bias check. Fourteen of the 23 compounds exhibited system biases less than 5% of FS, the limit contained in Method 6C. Seventeen of the compounds exhibited system biases less than 10% of FS. System bias is typically expressed as a function of FS. The least volatile compounds (the dichlorobenzenes) demonstrated positive biases, indicating that condensation within the sampling system is not a concern.

TABLE 1

| VOC Target Analytes | | |
|---|---|---|
| Chloromethane | Chloroform | Ethyl benzene |
| Vinyl chloride | 1,1,1-Trichlorethane | m/p-Xylenes |
| Bromomethane | Carbon tetrachloride | o-Xylene |
| Bromoethene | Benzene | Tribromomethane |
| 1,1-Dichloroethene | Trichloroethylene | Bromobenzene |
| 1,2-Dichloroethane | Toluene | 1,4-Dichlorobenzene |
| Dichloromethane | Tetrachloroethylene | 1,2-Dichlorobenzene |
| Hexane | Chlorobenzene | |

TABLE 2

Calibration Error as a Function of Full-Scale (Absolute Error)

| | | | "0% FS" | | | "30% FS" | | | "60% FS" | | | "90% FS" | | | |
|---|---|---|---|---|---|---|---|---|---|---|---|---|---|---|---|
| Analyte | Detector | $r^3$ | Actual (ppbv) | Calc. (ppbv) | Cal. Error (% FS) | Actual (ppbv) | Calc. (ppbv) | Cal. Error (% FS) | Actual (ppbv) | Calc. (ppbv) | Cal. Error (% FS) | Actual (ppbv) | Calc. (ppbv) | Cal. Error (% FS) | Max Cal Error |
| Chloromethane | FID | 0.993 | 0 | 3.2 | 3.2 | 30.5 | 25.8 | −4.6 | 60.9 | 60.7 | −0.2 | 91.4 | 93.1 | 1.7 | 4.6 |
| Vinyl chloride | FID | 0.998 | 0 | 1.7 | 1.7 | 31.0 | 28.5 | −2.5 | 62.1 | 62.0 | −0.1 | 93.1 | 94.0 | 0.9 | 2.5 |
| Bromomethane | FID | 0.993 | 0 | 2.9 | 2.9 | 30.4 | 27.1 | −3.2 | 60.7 | 58.3 | −2.4 | 91.1 | 93.7 | 2.7 | 3.2 |

TABLE 2-continued

Calibration Error as a Function of Full-Scale (Absolute Error)

|  |  |  | "0% FS" | | | "30% FS" | | | "60% FS" | | | "90% FS" | | | |
| --- | --- | --- | --- | --- | --- | --- | --- | --- | --- | --- | --- | --- | --- | --- | --- |
| Analyte | Detector | $r^3$ | Actual (ppbv) | Calc. (ppbv) | Cal. Error (% FS) | Actual (ppbv) | Calc. (ppbv) | Cal. Error (% FS) | Actual (ppbv) | Calc. (ppbv) | Cal. Error (% FS) | Actual (ppbv) | Calc. (ppbv) | Cal. Error (% FS) | Max Cal Error |
| Bromoethene | FID | 0.996 | 0 | 2.4 | 2.4 | 30.2 | 26.9 | −3.3 | 60.5 | 59.7 | −0.7 | 90.7 | 92.3 | 1.6 | 3.3 |
| 1,1-Dichloroethene | FID | 0.992 | 0 | 3.3 | 3.3 | 30.1 | 25.6 | −4.5 | 60.2 | 59.4 | −0.9 | 90.4 | 92.5 | 2.1 | 4.5 |
| 1,2-Dichloroethene | FID | 0.995 | 0 | 2.6 | 2.6 | 30.1 | 26.7 | −3.4 | 60.2 | 59.3 | −0.9 | 90.4 | 92.1 | 1.7 | 3.4 |
| Dichloromethane | FID | 0.991 | 0 | 3.5 | 3.5 | 30.0 | 25.2 | −4.8 | 60.0 | 59.2 | −0.8 | 90.0 | 92.2 | 2.2 | 4.8 |
| Hexane | FID | 0.996 | 0 | 2.4 | 2.4 | 30.1 | 26.8 | −3.3 | 60.2 | 59.7 | −0.6 | 90.4 | 91.9 | 1.5 | 3.3 |
| Chloroform | ECD | 0.999 | 0 | 0.0 | 0.0 | 30.0 | 29.3 | −0.7 | 60.0 | 61.5 | 1.5 | 90.0 | 89.3 | −0.7 | 1.5 |
| 1,1,1-Trichloroethane | ECD | 0.996 | 0 | −2.1 | −2.1 | 30.0 | 32.0 | 2.0 | 60.0 | 62.2 | 2.2 | 90.0 | 87.9 | −2.2 | 2.2 |
| Carbon tetrachloride | ECD | 1.000 | 0 | 0.4 | 0.4 | 30.2 | 29.3 | −1.0 | 60.5 | 61.2 | 0.7 | 90.7 | 90.6 | −0.2 | 1.0 |
| Benzene | FID | 0.994 | 0 | 2.8 | 2.8 | 30.0 | 26.3 | −3.7 | 60.0 | 59.0 | −1.0 | 90.0 | 91.9 | 1.9 | 3.7 |
| Trichloroethylene | ECD | 1.000 | 0 | 0.5 | 0.5 | 30.1 | 29.2 | −0.9 | 60.2 | 60.6 | 0.4 | 90.4 | 90.4 | 0.0 | 0.9 |
| Toluene | FID | 0.992 | 0 | 3.4 | 3.4 | 30.2 | 25.7 | −4.5 | 60.5 | 59.4 | −1.1 | 90.7 | 92.9 | 2.2 | 4.5 |
| Tetrachloroethylene | ECD | 0.907 | 0 | 11.8 | 11.8 | 30.1 | 13.7 | −16.5 | 60.2 | 57.8 | −2.4 | 90.4 | 97.4 | 7.1 | 16.5 |
| Chlorobenzene | FID | 0.990 | 0 | 3.7 | 3.7 | 30.1 | 25.4 | −4.8 | 60.2 | 58.6 | −1.6 | 90.4 | 93.0 | 2.7 | 4.8 |
| Ethyl benzene | FID | 0.996 | 0 | 2.4 | 2.4 | 30.1 | 27.3 | −2.8 | 60.2 | 58.8 | −1.4 | 90.4 | 92.2 | 1.9 | 2.8 |
| m/p-Xylenes | FID | 0.999 | 0 | 1.3 | 1.3 | 30.0 | 28.6 | −1.4 | 60.0 | 59.0 | −1.0 | 90.0 | 91.2 | 1.2 | 1.4 |
| o-Xylene | FID | 0.994 | 0 | 2.7 | 2.7 | 30.1 | 27.0 | −3.1 | 60.2 | 58.3 | −1.9 | 90.4 | 92.7 | 2.3 | 3.1 |
| Tribromomethane | ECD | 1.000 | 0 | −0.1 | −0.1 | 30.1 | 30.1 | −0.1 | 60.2 | 60.7 | 0.4 | 90.4 | 90.1 | −0.3 | 0.4 |
| Bromobenzene | FID | 0.990 | 0 | 3.7 | 3.7 | 30.1 | 25.8 | −4.3 | 60.2 | 57.8 | −2.4 | 90.4 | 93.4 | 3.0 | 4.3 |
| 1,4-Dichlorobenzene | FID | 0.988 | 0 | 3.9 | 3.9 | 30.0 | 25.4 | −4.6 | 60.0 | 57.4 | −2.6 | 90.0 | 93.3 | 3.3 | 4.6 |
| 1,2-Dichlorobenzene | FID | 0.988 | 0 | 3.9 | 3.9 | 30.2 | 26.0 | −4.2 | 60.5 | 57.2 | −3.3 | 90.7 | 94.3 | 3.6 | 4.2 |

Note:
Full-Scale (FS) is 100 ppbv
Values in bold meet Performance Specification 9 calibration criteria

TABLE 3

Calibration Error as a Function of Concentration (Relative Error)

|  |  |  | "0% FS" | | | "30% FS" | | | "60% FS" | | | "90% FS" | | | |
| --- | --- | --- | --- | --- | --- | --- | --- | --- | --- | --- | --- | --- | --- | --- | --- |
| Analyte | Detector | $r^3$ | Actual (ppbv) | Calc. (ppbv) | Cal. Error (Rel. %) | Actual (ppbv) | Calc. (ppbv) | Cal. Error (Rel. %) | Actual (ppbv) | Calc. (ppbv) | Cal. Error (Rel. %) | Actual (ppbv) | Calc. (ppbv) | Cal. Error (Rel. %) | Max Cal Error |
| Chloromethane | FID | 0.993 | 0 | 3.2 | N/A | 30.5 | 25.8 | −15.3 | 60.9 | 60.7 | −0.4 | 91.4 | 93.1 | 1.9 | 15.3 |
| Vinyl chloride | FID | 0.998 | 0 | 1.7 | N/A | 31.0 | 28.5 | −8.0 | 62.1 | 62.0 | −0.2 | 93.1 | 94.0 | 1.0 | 8.0 |
| Bromomethane | FID | 0.993 | 0 | 2.9 | N/A | 30.4 | 27.1 | −10.6 | 60.7 | 58.3 | −3.9 | 91.1 | 93.7 | 2.9 | 10.6 |
| Bromoethene | FID | 0.996 | 0 | 2.4 | N/A | 30.2 | 26.9 | −10.9 | 60.5 | 59.7 | −1.2 | 90.7 | 92.3 | 1.8 | 10.9 |
| 1,1-Dichloroethene | FID | 0.992 | 0 | 3.3 | N/A | 30.1 | 25.6 | −15.1 | 60.2 | 59.4 | −1.5 | 90.4 | 92.5 | 2.3 | 15.1 |
| 1,2-Dichloroethene | FID | 0.995 | 0 | 2.6 | N/A | 30.1 | 26.7 | −11.4 | 60.2 | 59.3 | −1.5 | 90.4 | 92.1 | 1.9 | 11.4 |

TABLE 3-continued

Calibration Error as a Function of Concentration (Relative Error)

| Analyte | Detector | $r^3$ | "0% FS" Actual (ppbv) | "0% FS" Calc. (ppbv) | "0% FS" Cal. Error (Rel. %) | "30% FS" Actual (ppbv) | "30% FS" Calc. (ppbv) | "30% FS" Cal. Error (Rel. %) | "60% FS" Actual (ppbv) | "60% FS" Calc. (ppbv) | "60% FS" Cal. Error (Rel. %) | "90% FS" Actual (ppbv) | "90% FS" Calc. (ppbv) | "90% FS" Cal. Error (Rel. %) | Max Cal Error |
|---|---|---|---|---|---|---|---|---|---|---|---|---|---|---|---|
| Dichloromethane | FID | 0.991 | 0 | 3.5 | N/A | 30.0 | 25.2 | −16.0 | 60.0 | 59.2 | −1.4 | 90.0 | 92.2 | 2.4 | 16.0 |
| Hexane | FID | 0.996 | 0 | 2.4 | N/A | 30.1 | 26.8 | −11.0 | 60.2 | 59.7 | −1.0 | 90.4 | 91.9 | 1.7 | 11.0 |
| Chloroform | ECD | 0.999 | 0 | 0.0 | N/A | 30.0 | 29.3 | −2.4 | 60.0 | 61.5 | 2.5 | 90.0 | 89.3 | −0.8 | 2.5 |
| 1,1,1-Trichloroethane | ECD | 0.996 | 0 | −2.1 | N/A | 30.0 | 32.0 | 6.6 | 60.0 | 62.2 | 3.7 | 90.0 | 87.9 | −2.4 | 6.6 |
| Carbon tetrachloride | ECD | 1.000 | 0 | 0.4 | N/A | 30.2 | 29.3 | −3.2 | 60.5 | 61.2 | 1.2 | 90.7 | 90.6 | −0.2 | 3.2 |
| Benzene | FID | 0.994 | 0 | 2.8 | N/A | 30.0 | 26.3 | −12.3 | 60.0 | 59.0 | −1.6 | 90.0 | 91.9 | 2.1 | 12.3 |
| Trichloroethylene | ECD | 1.000 | 0 | 0.5 | N/A | 30.1 | 29.2 | −3.1 | 60.2 | 60.6 | 0.7 | 90.4 | 90.4 | 0.0 | 3.1 |
| Toluene | FID | 0.992 | 0 | 3.4 | N/A | 30.2 | 25.7 | −14.8 | 60.5 | 59.4 | −1.8 | 90.7 | 92.9 | 2.4 | 14.8 |
| Tetrachloroethylene | ECD | 0.907 | 0 | 11.8 | N/A | 30.1 | 13.7 | −54.7 | 60.2 | 57.8 | −4.0 | 90.4 | 97.4 | 7.8 | 54.7 |
| Chlorobenzene | FID | 0.990 | 0 | 3.7 | N/A | 30.1 | 25.4 | −15.8 | 60.2 | 58.6 | −2.7 | 90.4 | 93.0 | 3.0 | 15.8 |
| Ethyl benzene | FID | 0.996 | 0 | 2.4 | N/A | 30.1 | 27.3 | −9.4 | 60.2 | 58.8 | −2.3 | 90.4 | 92.2 | 2.1 | 9.4 |
| m/p-Xylenes | FID | 0.999 | 0 | 1.3 | N/A | 30.0 | 28.6 | −4.8 | 60.0 | 59.0 | −1.7 | 90.0 | 91.2 | 1.3 | 4.8 |
| o-Xylene | FID | 0.994 | 0 | 2.7 | N/A | 30.1 | 27.0 | −10.4 | 60.2 | 58.3 | −3.2 | 90.4 | 92.7 | 2.6 | 10.4 |
| Tribromomethane | ECD | 1.000 | 0 | 0.1 | N/A | 30.1 | 30.1 | −0.2 | 60.2 | 60.7 | 0.7 | 90.4 | 90.1 | −0.3 | 0.7 |
| Bromobenzene | FID | 0.990 | 0 | 3.7 | N/A | 30.1 | 25.8 | −14.3 | 60.2 | 57.8 | −4.0 | 90.4 | 93.4 | 3.4 | 14.3 |
| 1,4-Dichlorobenzene | FID | 0.988 | 0 | 3.9 | N/A | 30.0 | 25.4 | −15.3 | 60.0 | 57.4 | −4.4 | 90.0 | 93.3 | 3.7 | 15.3 |
| 1,2-Dichlorobenzene | FID | 0.988 | 0 | 3.9 | N/A | 30.2 | 26.0 | −13.9 | 60.5 | 57.2 | −5.5 | 90.7 | 94.3 | 4.0 | 13.9 |

Note:
Values in bold meet Performance Specification 9 calibration criteria

TABLE 4

Calibration Precision - Relative Percent Difference from Average

| | Chloromethane | Vinyl chloride | Bromomethane | Bromoethene | 1,1-Dichloroethene | 1,2-Dichloroethane | Dichloromethano | Hexane |
|---|---|---|---|---|---|---|---|---|
| Run 1 | −0.6 | −6.9 | −4.8 | −6.8 | −23.7 | −9.0 | −23.2 | −15.5 |
| Run 2 | 2.5 | 3.4 | 2.4 | 4.8 | 15.4 | 6.2 | 15.9 | 10.4 |
| Run 3 | −2.0 | 3.5 | 2.4 | 2.0 | 8.4 | 2.8 | 7.3 | 5.4 |

| | Benzene | Toluene | Chlorobenzene | Ethylbenzene | m.p-Xylenes | o-Xylene | Bromobenzene | 1,4-Dichlorobenzene |
|---|---|---|---|---|---|---|---|---|
| Run 1 | −83.6 | −8.5 | −4.4 | −6.9 | −9.2 | −2.2 | −0.1 | −1.6 |
| Run 2 | 8.7 | 3.6 | 1.2 | 7.1 | 4.1 | −0.4 | −2.4 | −1.2 |
| Run 3 | 4.9 | 4.9 | 3.2 | 4.9 | 5.1 | 2.7 | 2.6 | 2.8 |

| | 1,2-Dichlorobenzene | Chloroform | 1,1,1-Trichloroethane | Carbon tetrachloride | Trichloroethane | Tetrachloroethane | Tribromomethane |
|---|---|---|---|---|---|---|---|
| Run 1 | 6.0 | −24.4 | −16.2 | −17.3 | −17.1 | −10.6 | 5.5 |
| Run 2 | −5.6 | 15.5 | 10.2 | 10.7 | 10.5 | 5.9 | −3.9 |
| Run 3 | −0.4 | 8.9 | 6.0 | 6.6 | 6.6 | 4.7 | −1.6 |

TABLE 5

Sampling System Bias Check Results

|  | Chloromethane | Vinyl chloride | Bromomethane | Bromoethene | 1,1-Dichloroethene | 1,2-Dichloroethane | Dichloromethano | Hexane |
|---|---|---|---|---|---|---|---|---|
| Sampling System Bias (% F8) | −0.9 | −2.5 | 0.8 | −8.6 | −1.2 | 0.2 | −1.3 | −0.7 |
| Sampling System Bias (Rel %) | −2.8 | −8.0 | 2.8 | −5.3 | −4.1 | 0.6 | −4.3 | −2.2 |

|  | Benzene | Toluene | Chlorobenzene | Ethylbenzene | m.p-Xylenes | o-Xylene | Bromobenzene | 1,4-Dichlorobenzene |
|---|---|---|---|---|---|---|---|---|
| Sampling System Bias (% F8) | −0.4 | −6.5 | 3.9 | −8.0 | −26.0 | −13.8 | 11.4 | 16.8 |
| Sampling System Bias (Rel %) | −8.3 | −21.6 | 13.0 | −26.7 | −26.5 | −45.7 | 38.0 | 56.1 |

|  | 1,2-Dichlorobenzene | Chloroform | 1,1,1-Trichloroethane | Carbon tetrachloride | Trichloroethane | Tetrachloroethane | Tribromomethane |
|---|---|---|---|---|---|---|---|
| Sampling System Bias (% F8) | 20.8 | −0.6 | −8.5 | −3.3 | 0.6 | −0.2 | 18.3 |
| Sampling System Bias (Rel %) | 69.3 | −1.9 | −28.4 | −10.8 | 1.9 | −0.8 | 37.6 |

We claim:

1. A process for analyzing a waste gas stream to determine concentrations of volatile organic compounds contained in the waste gas stream, said process comprising:
   sampling the waste gas stream to establish a continuous waste gas flow through, in sequence, a waste gas line, a switching valve and a first vent line;
   periodically diverting a portion of the waste gas flow at the switching valve;
   feeding the diverted portion of the waste gas flow in a first direction through a sorbent in an organics concentrator, preferentially sorbing the volatile organic compounds on said sorbent, and venting, through a second vent line, the remaining waste gas essentially free of the volatile organic compounds;
   periodically discontinuing the feed of the diverted waste gas flow through the sorbent and feeding a carrier gas through the sorbent in a second direction, opposite said first direction, for desorbing the volatile organic compounds from the sorbent thus forming a concentrated gas sample;
   periodically feeding the concentrated gas sample to a gas chromatograph for analysis of the concentrated gas sample to determine concentrations of the volatile organic compounds;
   blending various amounts of at least one of the volatile organic compounds with a gaseous carrier to form calibration samples containing known, different concentrations of the at least one volatile organic compound;
   feeding the calibration samples through the sorbent in the organics concentrator for sorbing and desorbing of the calibration samples;
   feeding the calibration samples desorbed from the sorbent to the gas chromatograph for analysis and calibration of the apparatus.

2. The process of claim 1 wherein said sorbing is conducted at ambient temperature and said desorbing is with heating of the sorbent.

3. The process of claim 1 further comprising regulating the flow of diverted waste gas through the sorbent and the feed of calibration samples through the sorbent to the same constant gas flow rate.

4. The process of claim 1 wherein a gaseous blend of a plurality of the volatile compounds in known concentrations is blended with the gaseous carrier to form the calibration samples, each containing different concentrations of the plural volatile organic compounds.

5. The process of claim 1 wherein the calibration samples are fed to the organics concentrator through the switching valve.

6. The process of claim 1 wherein the calibration samples are introduced into a control valve located in the waste gas line at a point adjacent the waste gas stream, the control valve switching between a sampling position where the waste gas is admitted to the waste gas line with the calibration samples blocked therefrom and a calibration position where the calibration samples are admitted to the waste gas line with the exhaust gas blocked therefrom.

7. The process of claim 1 further comprising scrubbing the continuous waste gas flow to remove acidic gases.

8. An apparatus for periodic analysis of trace amounts of volatile organic compounds in a waste gas, comprising:
   a probe for extracting a sample from a stream of the waste gas;
   an organics concentrator containing a sorbent having preferential affinity for the volatile organic compounds;
   a waste gas line connecting said probe to a first vent line;
   a switching valve between said waste gas line and said first vent line for diverting, in a sampling mode, a portion of the waste gas flow to said vent to said organics concentrator, the waste gas portion flowing through said sorbent in a first direction, in said sampling mode, and exiting said organics concentrator through a second gas vent line;
   a source of a carrier gas for feeding the carrier gas through the sorbent in a second direction, opposite the first direction, to purge the volatile organic compounds from the sorbent thereby forming a gas sample stream;
   a gas chromatograph for receiving the gas sample stream and for analyzing the gas sample stream to determine concentrations of volatile organic compounds contained therein;
   a gas blender for blending at least one of the volatile organic compounds with a carrier gas to form a plurality of calibration gas streams containing different concentrations of the at least one volatile organic compounds; and a calibration gas line for feeding the calibration gas streams to said organics concentrator in a calibration mode.

9. The apparatus of claim 8 wherein said calibration gas line connects said gas blender to said switching valve.

10. The apparatus of claim 8 wherein said organics concentrator contains a heater for heating said sorbent during the purging of volatile organic compounds from the sorbent.

11. The apparatus of claim 8 further comprising a three-way valve in said waste gas line adjacent said probe and a system calibration line for feeding the calibration gas streams from said gas blender to said three-way valve.

12. The apparatus of claim 8 further comprising a sample pump in said waste gas line and a vacuum pump in said second vent line.

13. The apparatus of claim 8 further comprising a mass flow controller in said second vent line for controlling flow of the exhaust gas through said organics concentrator to a constant gas flow rate.

14. The apparatus of claim 8 further comprising, in said waste gas line, a heated filter for removing particulates from the waste gas and a gas scrubber for removing acid gases from the waste gas.

15. The apparatus of claim 8 wherein said gas chromatograph has a flame ionization detector, an electron capture detector and a chromatograph column which receives the gas sample stream, and wherein said gas chromatograph splits the gas sample stream exiting the chromatograph column to simultaneously feed portions of the gas sample stream to both the flame ionization detector and the electron capture detector.

16. The apparatus of claim 8 wherein said gas chromatograph has a mass selective detector.

* * * * *